(12) United States Patent
Horiuchi et al.

(10) Patent No.: US 9,700,271 B2
(45) Date of Patent: Jul. 11, 2017

(54) PORTABLE RADIOGRAPHIC IMAGE CAPTURING APPARATUS AND CASING

(71) Applicant: FUJIFILM Corporation, Tokyo (JP)

(72) Inventors: Hisatsugu Horiuchi, Ashigarakami-gun (JP); Takeyasu Kobayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/603,061

(22) Filed: Jan. 22, 2015

(65) Prior Publication Data

US 2015/0253441 A1    Sep. 10, 2015

(30) Foreign Application Priority Data

Mar. 10, 2014    (JP) .................................. 2014-045973

(51) Int. Cl.
*A61B 6/00* (2006.01)
*G01T 1/20* (2006.01)
*G03B 42/04* (2006.01)

(52) U.S. Cl.
CPC .......... *A61B 6/4405* (2013.01); *A61B 6/4233* (2013.01); *A61B 6/4283* (2013.01); *G01T 1/2018* (2013.01); *G03B 42/04* (2013.01)

(58) Field of Classification Search
CPC ... A61B 6/4405; A61B 6/4216; A61B 6/4283; A61B 6/4233; G01T 1/2018; G03B 42/04
USPC .................................................... 250/361 R
See application file for complete search history.

(56) References Cited

U.S. PATENT DOCUMENTS

| 4,594,008 A | * | 6/1986 | Affolter | G04B 39/02 368/276 |
| 2012/0217395 A1 | * | 8/2012 | Kobayashi | A61B 6/4291 250/336.1 |
| 2012/0314354 A1 | * | 12/2012 | Rayner | G06F 1/1656 361/679.01 |
| 2013/0051524 A1 | * | 2/2013 | Sato | A61B 6/5205 378/62 |

FOREIGN PATENT DOCUMENTS

| EP | 2128650 A1 | 12/2009 |
| JP | 6-1926 U | 1/1994 |
| JP | 8-298385 A | 11/1996 |
| JP | 9-89115 A | 3/1997 |
| JP | 2000-258541 A | 9/2000 |
| JP | 2001-189575 A | 7/2001 |

(Continued)

OTHER PUBLICATIONS

Japanese Office Action for Japanese Application No. 2014-045973, dated Jan. 24, 2017, with an English translation.

*Primary Examiner* — David Porta
*Assistant Examiner* — Gisselle Gutierrez
(74) *Attorney, Agent, or Firm* — Birch, Stewart, Kolasch & Birch, LLP

(57) ABSTRACT

A portable radiographic image capturing apparatus includes a casing having a front face including a top plate and a rear face. The rear face is fitted in the front face such that second sides of the rear face are disposed inside of first sides of the front face. Water-resistant members are disposed in corner portions that are formed in the front face. The second sides have ridges for pressing and elastically deforming the water-resistant members toward the top plate. The ridges have slanted outer side surfaces.

11 Claims, 12 Drawing Sheets

(56) References Cited

FOREIGN PATENT DOCUMENTS

| | | | |
|---|---|---|---|
| JP | 2003-258450 | A | 9/2003 |
| JP | 2008-42771 | A | 2/2008 |
| JP | 2008-180554 | A | 8/2008 |
| JP | 2012-181044 | A | 9/2012 |
| JP | 2012-253179 | A | 12/2012 |

* cited by examiner

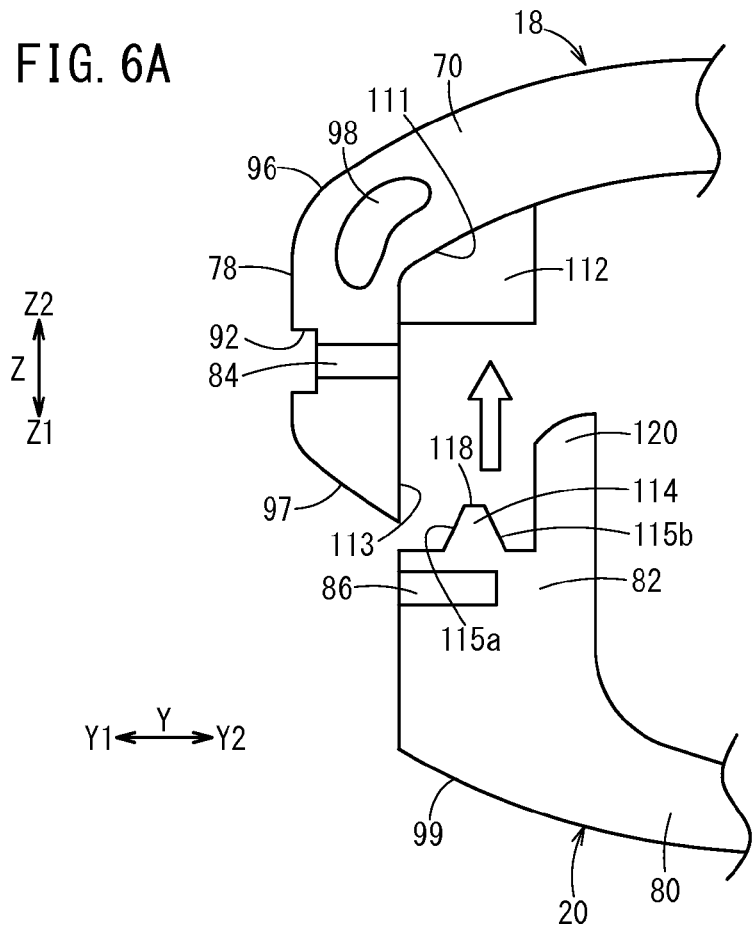
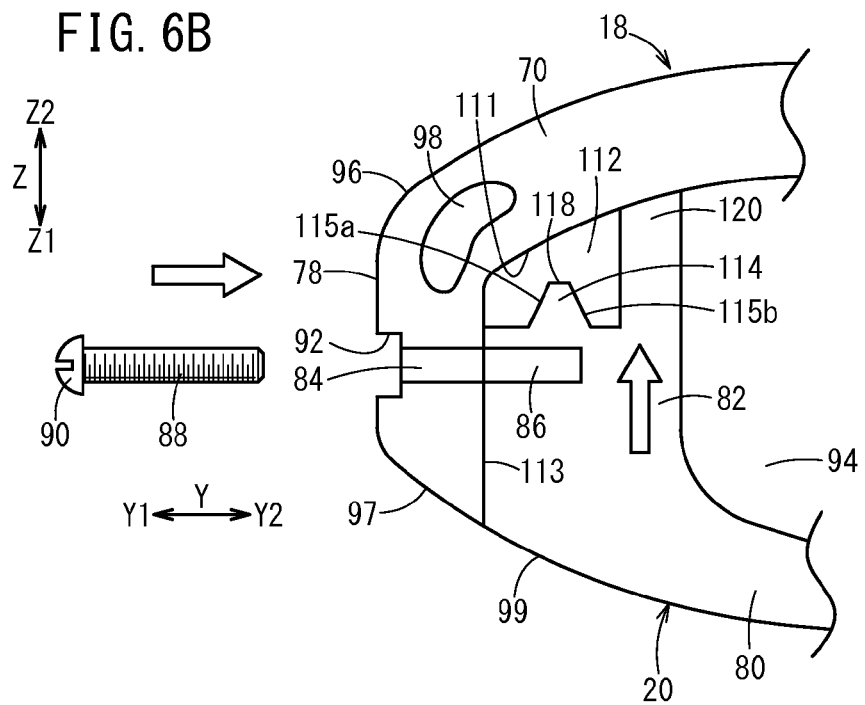

PORTABLE RADIOGRAPHIC IMAGE CAPTURING APPARATUS AND CASING

CROSS-REFERENCE TO RELATED APPLICATION

This application is based upon and claims the benefit of priority from Japanese Patent Application No. 2014-045973 filed on Mar. 10, 2014, the contents of which are incorporated herein by reference.

BACKGROUND OF THE INVENTION

Field of the Invention

The present invention relates to a casing that houses a radiation conversion panel for outputting image information on the basis of applied radiation, and a portable radiographic image capturing apparatus that includes the casing and the radiation conversion panel.

Description of the Related Art

Japanese Laid-Open Patent Publication No. 2000-258541, for example, discloses a radiographic image capturing apparatus for detecting radiation that has passed through a subject with a radiation conversion panel housed in a casing, converting the detected radiation into image information, and outputting the image information.

Japanese Laid-Open Patent Publication No. 2000-258541 reveals that an opening in a box-shaped casing is covered with a radiation-permeable cover. The cover and a side wall erected from an end of a bottom wall of the casing are fastened by screws along a thickness-wise direction (vertical direction) of the casing that extends from the cover to the bottom wall.

SUMMARY OF THE INVENTION

The radiographic image capturing apparatus, which is constructed as a portable radiographic image capturing apparatus, may occasionally be used in medical operation sites. In case that the portable radiographic image capturing apparatus is used in a medical operation site, the radiographic image capturing apparatus may possibly be splashed with body fluids such as blood. Therefore, the portable radiographic image capturing apparatus is required to be water-resistant.

The portable radiographic image capturing apparatus is of a flat shape having a front face that includes a top plate, which is opposite to a surface that is irradiated with radiation, and a rear face that is fitted in the front face. In case that the portable radiographic image capturing apparatus is inserted between the subject and a bed, the front face tends to become concave in a central region thereof under the load from the subject. With the front face being warped in this manner, a gap is created between an edge of the front face and a corresponding edge of the rear face, potentially reducing the water-resistant capability of the portable radiographic image capturing apparatus.

In case that attempts are made to reduce the size of the portable radiographic image capturing apparatus by reducing the size of the casing without changing the size of the radiation conversion panel, the space in the casing, which houses components other than the radiation conversion panel, is reduced to such an extent that it becomes difficult to maintain a space for housing a water-resistant member therein. Consequently, it is not easy to ensure the water-resistant capability of the portable radiographic image capturing apparatus.

The present invention aims to solve the aforementioned problems, and an object of the present invention is to provide a portable radiographic image capturing apparatus and a casing that are highly water-resistant.

The present invention pertains to a casing that houses a radiation conversion panel for outputting image information on the basis of radiation applied thereto, and also pertains to a portable radiographic image capturing apparatus including the radiation conversion panel, and the casing.

To achieve the above object, the casing comprises a front face including a planar top plate disposed opposite to an irradiation surface of the radiation conversion panel, and a rear face that is fitted in the front face. The front face includes a first side that extends from an end of the top plate toward the rear face. The rear face includes a bottom plate disposed opposite to the planar top plate and the radiation conversion panel, and a second side that extends from an end of the bottom plate toward the top plate, the rear face being fitted in the front face such that the second side is positioned inside of the first side.

A water-resistant member is disposed in a cavity inside of a junction between the top plate and the first side of the front face. The second side has a ridge for pressing and deforming the water-resistant member toward the top plate. The ridge has a slanted outer side surface.

According to the present invention, the ridge includes the slanted outer side surface, which presses the water-resistant member toward the top plate and deforms the water-resistant member. More specifically, the ridge has a slanted or sloping outer side surface, and the water-resistant member, which is disposed in the corner portion inside of a junction between the top plate and the first side, is compressed toward the top plate due to the gradient of the outer side surface. Therefore, the water-resistant member is capable of maintaining the water-resistant condition of the casing, even though the water-resistant member is comparatively thin-walled and simple in structure.

The overall thickness of the portable radiographic image capturing apparatus can be reduced by reducing the thickness of the water-resistant member. Consequently, in case that radiographic images of a patient who serves as a subject lying on a bed are captured using the portable radiographic image capturing apparatus, the portable radiographic image capturing apparatus can easily be inserted between the patient and the bed with the front face thereof facing toward the patient. Accordingly, the ability to insert the portable radiographic image capturing apparatus is excellent.

According to Japanese Laid-Open Patent Publication No. 2000-258541, as described above, the cover and the side wall, which are erected from the end of the bottom wall of the casing, are fastened by screws along a thickness-wise direction (vertical direction) of the casing. Consequently, in case that radiographic images of a patient who serves as a subject lying on a bed are captured, the screws or the screw holes may become caught on the patient at the time that the portable radiographic image capturing apparatus is inserted between the patient and the bed in such a manner that the cover thereof faces toward the patient.

According to the present invention, the first and second sides are kept in an interfitted condition by the fastener along the direction of the top plate and the bottom plate. Since the first and second sides are fastened together by the fasteners in a lateral or horizontal direction, which is perpendicular to the thickness-wise direction of the casing, the top plate that is placed in contact with the subject is free of surface irregularities. Consequently, the portable radiographic image capturing apparatus can be inserted between the patient and the bed without causing the fasteners to become caught on the subject. Owing thereto, the ability to insert the portable radiographic image capturing apparatus is increased.

Further, inasmuch as the outer side surface of the ridge is slanted, as described above, in case that the first and second sides are fastened together by the fasteners, a reaction force, which is caused by a fastening force that acts on the first and second sides, is exerted on the water-resistant member. Consequently, the water-resistant member is compressed effectively toward the front face. Therefore, the water resistance of the casing is increased by fastening the first and second sides with the fasteners.

According to the present invention, a casing support may be disposed near the water-resistant member and extend from the bottom plate toward the top plate. In case that the ridge presses the water-resistant member toward the top plate, the casing support is brought into contact with the front face, thereby limiting the amount by which the water-resistant member is compressed by the ridge to a position corresponding to a prescribed compressed thickness. Even in case that the front face is placed under the weight of the subject's body, deformation of the front face is prevented from adversely affecting the amount by which the water-resistant member is compressed.

In case that the angle of the slanted outer side surface is in a range from 30° to 60°, the ridge can effectively compress the water-resistant member. Assuming that the above angle lies in a range from 30° to 60°, a force component directed toward the front face of the pressing force, which is applied from the ridge to the water-resistant member, is increased, and therefore, the ridge can effectively compress the water-resistant member.

In case that the width of a portion of the ridge that is held in contact with the water-resistant member is in a range from 0.2 mm to 3.0 mm, the ridge can effectively compress the water-resistant member. Since the width of the water-resistant member is comparatively small, it is possible to enlarge the image-capturing area of the portable radiographic image capturing apparatus up to positions near the side edges of the casing.

In case that the above width is 0.2 mm or greater, the area of the ridge that presses the water-resistant member is increased, so that the ridge appropriately compresses the water-resistant member to achieve a desired water-resistant capability. On the other hand, in case that the width is 3.0 mm or less, it is easier for a space to be provided so that the ridge can be accommodated in a storage space in the interior of the casing.

According to the present invention, the portable radiographic image capturing apparatus may further comprise an external water-resistant member that covers an exposed portion of the fastener. The external water-resistant member is effective to conceal the fastener as well as to increase the water resistance of the casing.

The top plate preferably is made of carbon or a resin permeable to radiation. In case that the top plate is made of carbon or a resin, the casing can be constructed in a simple shape, the casing is more permeable to, radiation, and the thickness of the casing can effectively be reduced.

In case that the water-resistant member, which is disposed in the corner portion inside of a junction between the top plate and the first side, is an elastic member, the water-resistant member can easily be compressed by the ridge.

The above and other objects, features, and advantages of the present invention will become more apparent from the following description in case that taken in conjunction with the accompanying drawings in which preferred embodiments of the present invention are shown by way of illustrative example.

BRIEF DESCRIPTION OF THE DRAWINGS

FIG. 6A is an enlarged fragmentary cross-sectional view of the side region, showing a state before a water-resistant member is compressed;

FIG. 6B is an enlarged fragmentary cross-sectional view of the side region, showing a state after the water-resistant member is compressed by a ridge;

DESCRIPTION OF THE PREFERRED EMBODIMENTS

Portable radiographic image capturing apparatus and casings according to preferred embodiments of the present invention will be described in detail below with reference to the accompanying drawings.

Structure of Electronic Cassette and Casing

Figure 1:
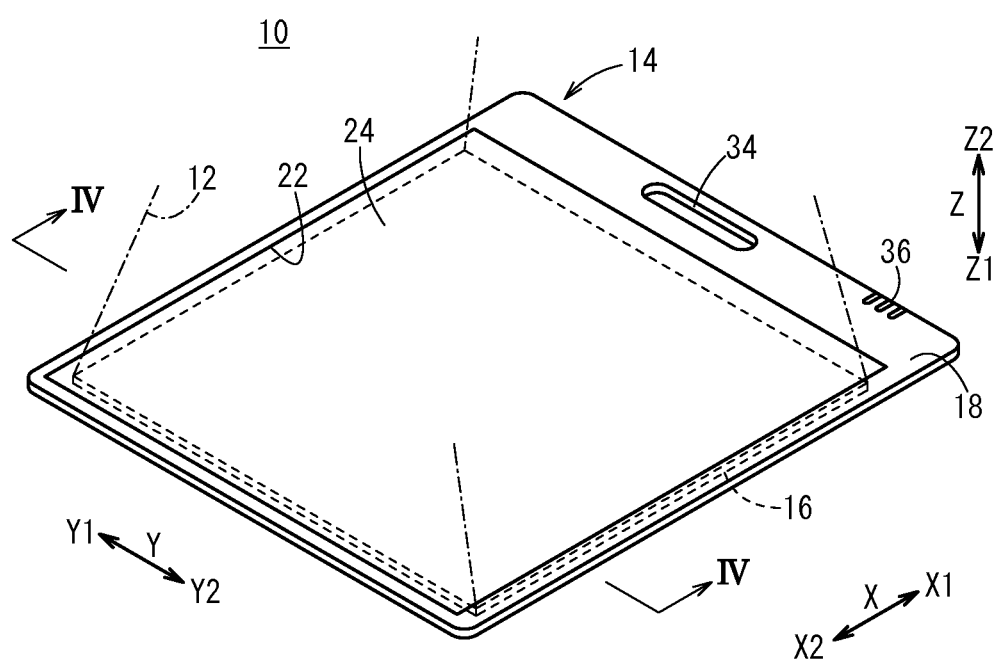
FIG. 1 is a perspective view of an electronic cassette according to an embodiment of the present invention, showing a front face thereof.
Figure 2:
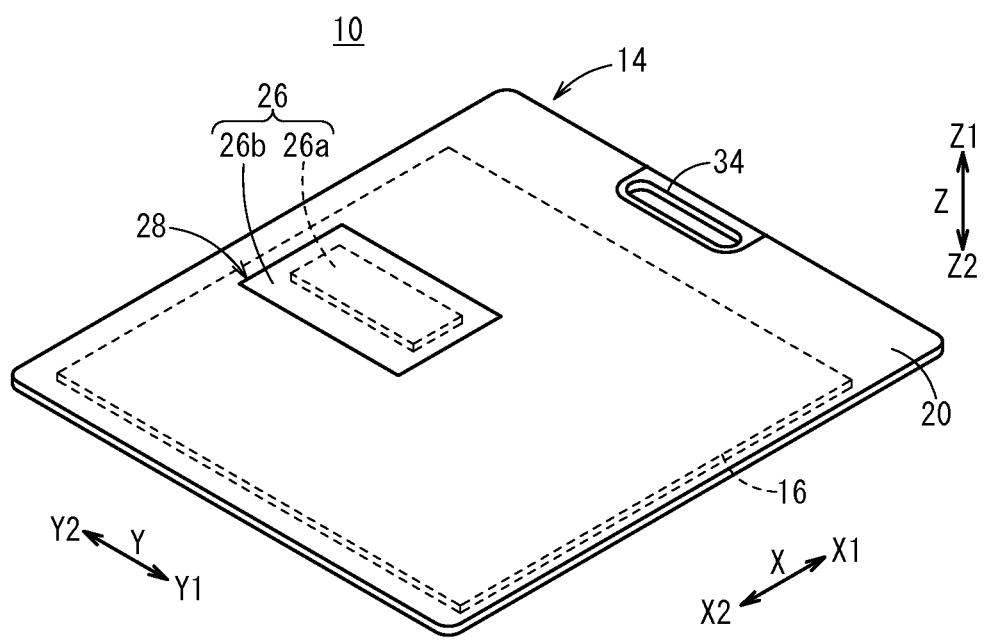
FIG. 2 is a perspective view of the electronic cassette shown in FIG. 1, showing a rear face thereof.
Figure 3:
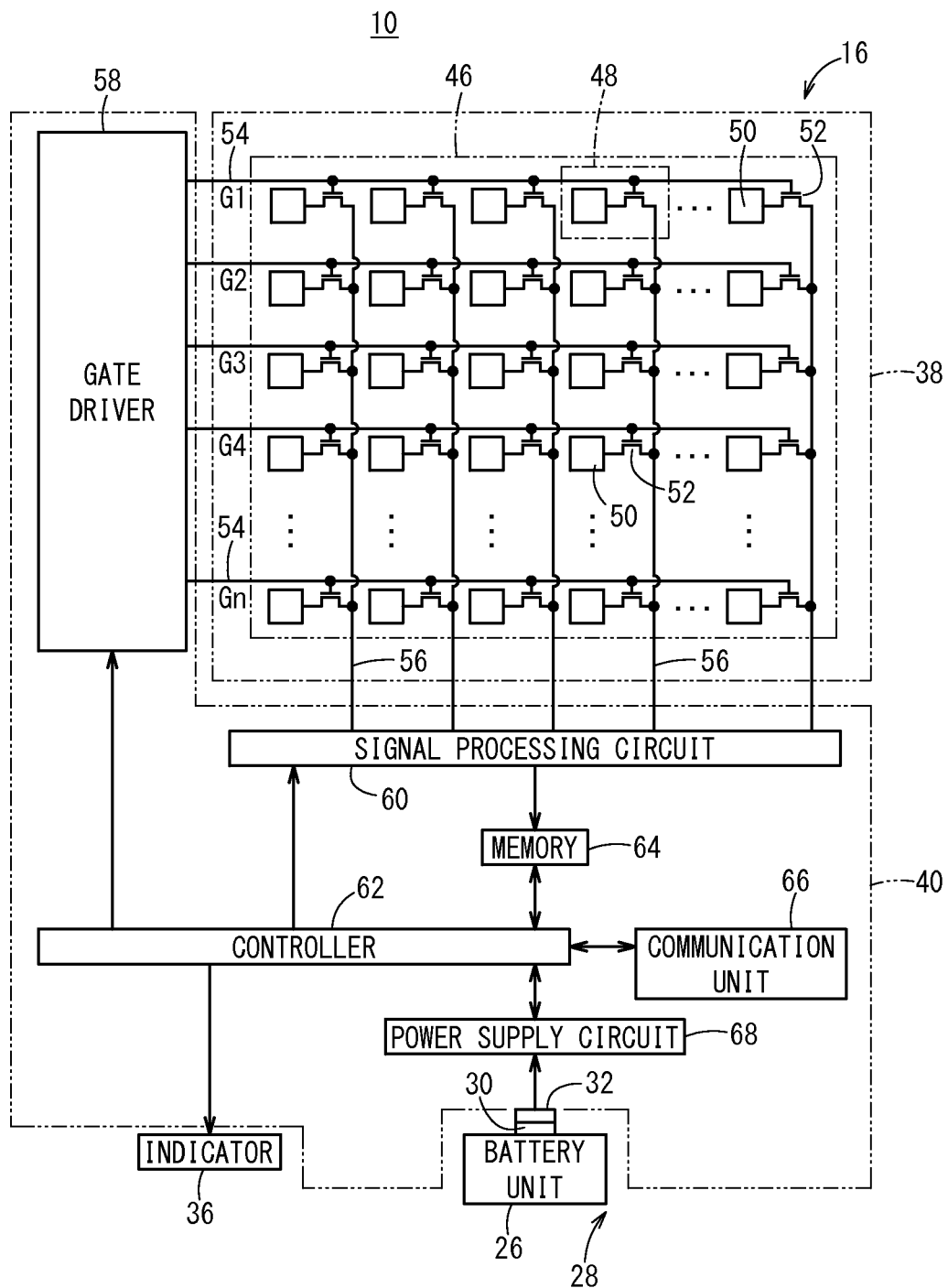
FIG. 3 is an electric block diagram of the electronic cassette shown in FIGS. 1 and 2.

As shown in FIGS. 1 through 3, an electronic cassette 10, which serves as a portable radiographic image capturing apparatus according to an embodiment of the present invention, includes a portable casing 14, which is permeable to applied radiation 12, and an image detector 16 that is housed in the casing 14. The image detector 16 converts radiation 12 into image information and outputs the image information.

Figure 4:
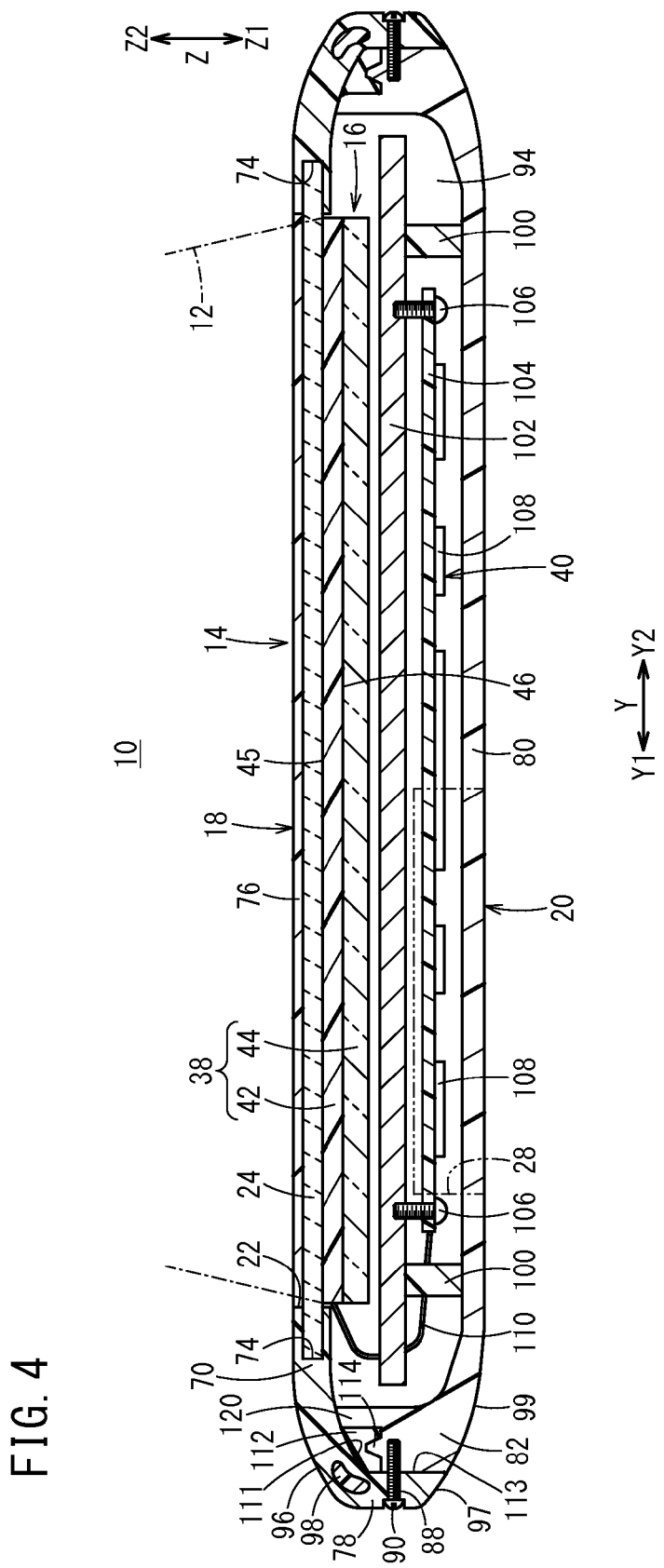
FIG. 4 is an enlarged cross-sectional view taken along line IV-IV of FIG. 1.
Figure 5:
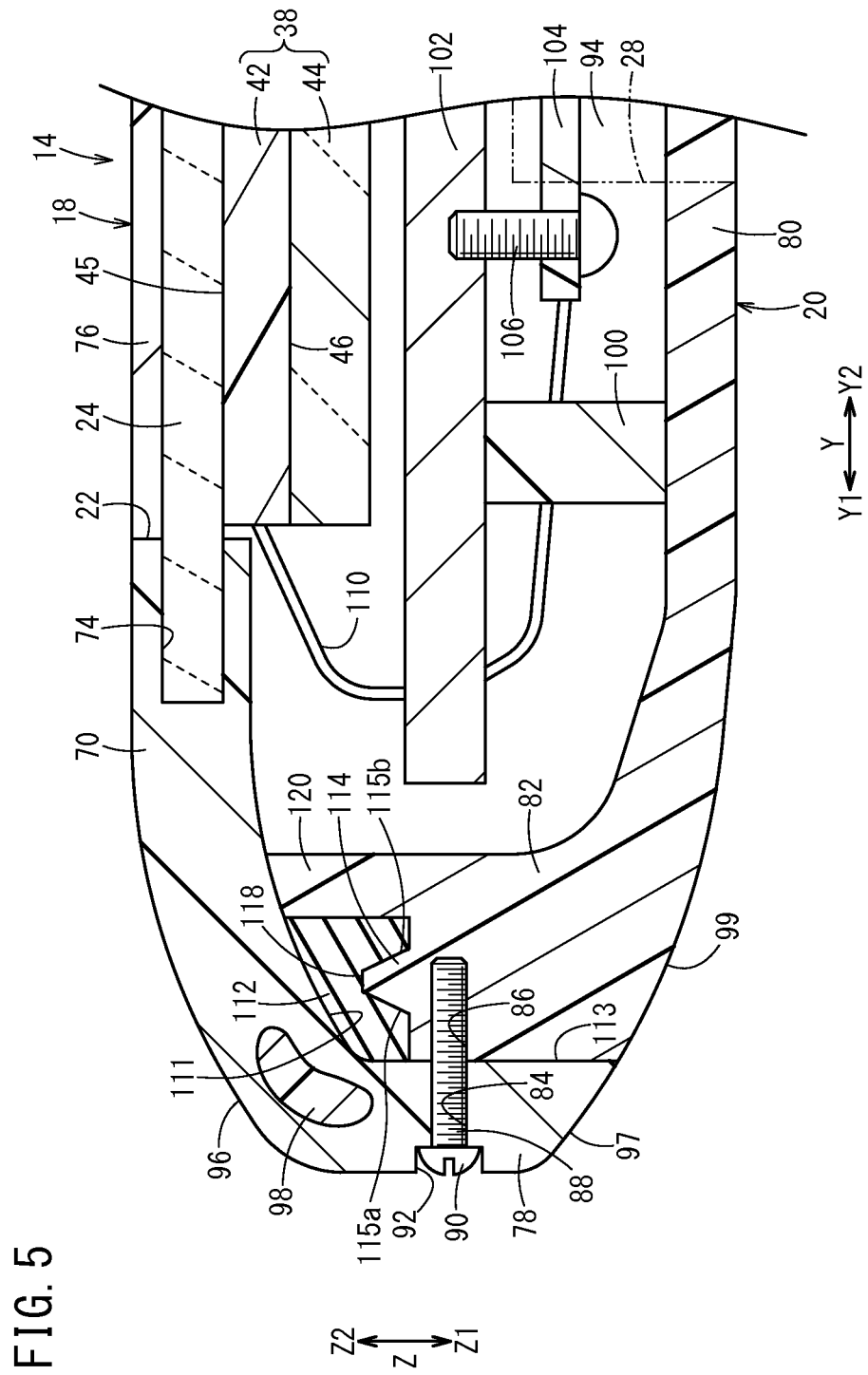
FIG. 5 is an enlarged fragmentary cross-sectional view of a side region of a casing according to the embodiment.

The casing 14 according to the present embodiment includes a front face 18 that is irradiated with radiation 12, and a rear face 20 that is fitted in the front face 18. The front face 18 has a centrally defined rectangular opening 22. The opening 22 is fitted with a planar top plate 24, which is lightweight and highly rigid, and is made of carbon or a resin that is highly permeable to radiation 12. As shown in FIGS. 4 and 5, the top plate 24 is disposed opposite to a radiation conversion panel 38.

The front face 18 is disposed in the direction of the arrow Z2, whereas the rear face 20 is disposed in the direction of the arrow Z1. Radiation 12 is applied to the top plate 24 within a range corresponding to the opening 22.

The casing 14, which is lightweight as a whole, functions as an electromagnetic shield. More specifically, the portion of the casing 14 other than the top plate 24 preferably is made of an electrically conductive resin, for example. In case that the top plate 24 is made of a resin, the resin preferably is an electrically conductive resin. The casing 14, which is arranged in the foregoing manner, is capable of preventing electromagnetic noise from entering the electronic cassette 10, and also prevents electromagnetic noise from being radiated outside of the electronic cassette 10.

A battery unit 26 is mounted on the rear face 20, which is disposed opposite to the front face 18. The battery unit 26 includes a battery 26a for supplying electric power to the image detector 16, and a box-shaped battery case 26b in which the battery 26a is accommodated. The battery unit 26 is removably mounted in a battery mount region 28 provided on the rear face 20.

In FIG. 2, the battery unit 26 is shown as being mounted in the battery mount region 28. The battery unit 26 is locked against removal from the battery mount region 28 by a non-illustrated lock mechanism.

As shown in FIGS. 4 and 5, the battery mount region 28 is in the form of a recess, which forms a hollow in a portion of the rear face 20 facing toward the front face 18. The battery mount region 28 is substantially the same shape and size as the battery unit 26, so that the battery unit 26 can be fitted snugly in the battery mount region 28. Therefore, the depth of the battery mount region 28 along the direction of the arrow Z also is substantially the same as the thickness of the battery unit 26.

In case that the battery unit 26 is mounted in the battery mount region 28, the surface of the battery unit 26 that faces in the direction of the arrow Z1 is exposed outwardly and lies substantially flush with the rear face 20. In FIGS. 4 and 5, the battery mount region 28 is illustrated by the two-dot-and-dash line.

As shown in FIG. 3, the battery unit 26 has a connector 30. The battery mount region 28 has a socket 32 for receiving the connector 30. In case that the battery unit 26 is mounted in the battery mount region 28, the connector 30 is fitted in the socket 32 and is connected electrically to the socket 32. The battery 26a supplies electric power through the connector 30 and the socket 32 to the image detector 16, whereby the image detector 16 is energized.

As shown in FIGS. 1 and 2, the casing 14 is in the shape of a rectangular parallelepiped, and has a size in conformity with International Standard ISO4090:2001, which is essentially similar to the sizes of IP cassettes and CR cassettes. The electronic cassette 10 is removably set in a holder of an upright or recumbent image-capturing table, which supports a subject, e.g., a patient, thereon, so that the front face 18 is positioned opposite to a non-illustrated radiation source that emits radiation 12. Since the size of the electronic cassette 10 is essentially similar to the sizes of film cassettes, IP cassettes, and CR cassettes, the electronic cassette 10 can be mounted on existing image-capturing tables on which such film cassettes, IP cassettes, and CR cassettes are used.

The electronic cassette 10 may also be used alone on patients who are unable to move on their own, e.g., patients lying on beds, aged patients on beds, emergency patients on beds, etc. In such applications, the electronic cassette 10 is inserted between the bed and the patient on the bed, with the front face 18 of the electronic cassette 10 facing toward the patient.

The electronic cassette 10 need not necessarily be of a size in conformity with International Standard ISO4090:2001.

The casing 14 includes a handle 34 on a side thereof facing in the direction of the arrow X1. An operator of the electronic cassette 10, such as a doctor, a radiologist, or the like, grips the handle 34 to carry the electronic cassette 10. The casing 14 also has an indicator 36 composed of LEDs or the like disposed near the handle 34 on the front face 18, for visually indicating in case that a power supply of the electronic cassette 10 is turned on and off, as well as indicating the remaining energy level of the battery 26a.

As shown in FIG. 3, the image detector 16 includes a radiation conversion panel 38 and a circuit section 40.

As shown in FIGS. 4 and 5, the radiation conversion panel 38 includes a thin-film-transistor (TFT) active matrix board 42, which is made of glass, and a phosphor scintillator 44 for converting radiation 12 into visible light. The TFT active matrix board 42 will hereinafter be referred to simply as a TFT board 42.

The scintillator 44 is made of thallium-added cesium iodide (CsI:Tl), terbium-added gadolinium oxysulfide (Gd2O2S:Tb, GOS), or the like. In case that radiation 12 is applied to an upper surface of the TFT board 42, which serves as an irradiation surface 45 of the radiation conversion panel 38, and passes through the TFT board 42, the scintillator 44 converts the applied radiation 12 into visible light, the intensity of which depends on the dose of radiation 12.

A lower surface of the TFT board 42, which faces toward the scintillator 44, serves as an image-capturing area 46 that includes a matrix of pixels 48. The pixels 48 are arranged, as shown in FIG. 3, in n rows, which are spaced vertically at a prescribed pitch, and m columns, which are spaced horizontally at a prescribed pitch, where n and m each represent an integer of 2 or greater. For example, n=m≈2000. The pixels 48 are arranged in a square array as shown in FIG. 3, however, the pixels 48 may also be arranged in a honeycomb array.

Each of the pixels 48 comprises a photoelectric transducer 50 for generating and storing electric charges (electron-hole pairs) depending on visible light applied from the scintillator 44, and a TFT (thin-film transistor) 52 that serves as a switching element.

The photoelectric transducer 50 has a structure including a semiconductor layer (e.g., PIN type) for generating electric charges, and an upper electrode and a lower electrode, which are disposed respectively on upper and lower surfaces of the semiconductor layer. The TFT 52 is connected to the lower electrode, whereas a non-illustrated bias line is connected to the upper electrode. In the image-capturing area 46, there are as many bias lines as the number of rows (n rows) of pixels 48. The bias lines are connected as branch lines to a bus line that is connected to a non-illustrated bias power supply. A bias voltage is applied from the bias power supply through the bus line and the bias line to the upper electrode of the photoelectric transducer 50. Upon application of the bias voltage, an electric field is developed in the semiconductor layer, thereby causing an electric charge (electron-hole pair) to be generated in the semiconductor layer by photoelectric conversion, which moves to the upper and lower electrodes, one of which is of a positive polarity and the other of which is of a negative polarity. As a result, the photoelectric transducer 50 stores the electric charge.

The TFT 52 has a gate electrode connected to a scanning line 54, a source electrode connected to a signal line 56, and a drain electrode connected to the photoelectric transducer 50. The scanning lines 54 and the signal lines 56 are arranged in a grid pattern. In the image-capturing area 46, there are as many scanning lines 54 as the number of rows (n rows) of pixels 48. Each of the scanning lines 54 is shared by one row of pixels 48. There are also as many signal lines 56 as the number of columns (m columns) of pixels 48. Each of the signal lines 56 is shared by one column of pixels 48. The scanning lines 54 are connected to a gate driver 58 in the circuit section 40, whereas the signal lines 56 are connected to a signal processing circuit 60 in the circuit section 40.

The circuit section 40 includes, in addition to the gate driver 58 and the signal processing circuit 60, a controller 62, a memory 64, a communication unit 66, and a power supply circuit 68.

The gate driver 58 is controlled by the controller 62 to energize and de-energize the TFTs 52, such that the image detector 16 operates selectively in different modes. The different modes include a storing mode for storing electric charges (hereinafter also referred to as "signal charges") depending on the dose of radiation 12 having reached the radiation conversion panel 38 in the pixels 48, a reading mode for reading the signal charges stored in the pixels 48, and a resetting mode for flushing out unwanted charges stored in the pixels 48.

In the storing mode, the TFTs 52 are turned off or de-energized, and signal charges are stored in the pixels 48 while the TFTs 52 are de-energized. In the reading mode, the gate driver 58 generates gate pulses G1 through Gn successively at prescribed intervals for energizing the TFTs 52 simultaneously along the respective rows, thereby activating the scanning lines 54 one at a time, and hence turning on the TFTs 52 connected to the scanning lines 54 one row at a time. In case that the TFTs 52 are turned on, the signal charges stored in the photoelectric transducers 50 of the pixels 48 are read into the signal lines 56, from which the signal charges are input to the signal processing circuit 60.

The signal processing circuit 60 includes integrating amplifiers, CDS circuits, a multiplexer, and an A/D converter. The integrating amplifiers and the CDS circuits are connected individually to the signal lines 56. The integrating amplifiers integrate signal charges that are input from the signal lines 56, convert the integrated signal charges into analog voltage signals, and output the analog voltage signals. The CDS circuits perform correlative double sampling on the voltage signals from the integrating amplifiers, and hold the voltage signals for a prescribed period of time. Using electronic switches, the multiplexer selects the CDS circuits one at a time. The CDS circuits are assigned respectively to the columns and are connected in parallel with each other, and the multiplexer inputs voltage signals, which are output from the selected CDS circuits, in a serial stream to the A/D converter. The A/D converter converts the analog voltage signals, which are input from the multiplexer, into digital pixel values, and outputs the digital pixel values to the memory 64. The memory 64 stores the digital pixel values in association with respective coordinates of the pixels 48.

Therefore, each time that the gate driver 58 supplies one of the gate pulses G1 through Gn in order to turn on a corresponding row of TFTs 52, the memory 64 stores the pixel values from one row of pixels 48. After the signal charges from all of the rows of pixels 48 have been read out of the image-capturing area 46, the memory 64 stores image information representing a single radiographic image captured by the image-capturing area 46. The image information is read out of the memory 64, processed by the controller 62 according to prescribed image processing sequences, and thereafter, the image information is output to an external apparatus such as a console or the like through the communication unit 66. In this manner, a radiographic image of the patient is detected.

The communication unit 66 includes an antenna and an oscillating circuit for generating electromagnetic waves for enabling wireless communication. The communication further includes a socket for enabling wired communication. Hence, the communication unit 66 is compatible with both wireless and wired communication modes. The communication unit 66 exchanges radiographic images and image-capturing conditions, such as an irradiation time for the radiation 12, etc., with an external apparatus such as a console or the like. The wireless communication mode includes not only communication via electromagnetic waves, but may also include optical communication using infrared rays or the like.

The power supply circuit 68 is connected to the battery unit 26 by the socket 32 and the connector 30 of the battery mount region 28. The power supply circuit 68 is controlled by the controller 62 in order to convert electric power under a prescribed voltage from the battery unit 26 into electric power under voltages that are suitable for various parts of the image detector 16, and to supply such voltages to the various parts of the image detector 16. The power supply circuit 68 also monitors the voltage level of electric power supplied from the battery unit 26 in order to detect the remaining energy level of the battery 26a, and outputs the detected remaining energy level to the controller 62. The controller 62 changes the indication on the indicator 36 depending on the remaining energy level of the battery 26a, which is sent from the power supply circuit 68. The power supply circuit 68 may be connected to a power supply cable that extends from a non-illustrated external power supply, so that the power supply circuit 68 can be supplied with electric power from the external power supply, rather than from the battery unit 26.

As shown in FIG. 4, the front face 18 of the casing 14 includes a front face cover 70 with the opening 22 defined therein. The front face cover 70 has grooves 74 defined in edges thereof, which open into the opening 22 and extend along the direction of the arrow Y. The top plate 24 is fixed to the front face cover 70 by edges thereof being fitted into the grooves 74. In case that the opening 22 is fitted with the top plate 24 fixed to the front face cover 70 in this manner, a step is created between the upper surface of the top plate 24 and the upper surface of the front face cover 70. In order to eliminate the step, a protective film 76 of resin, which is permeable to radiation 12, is applied to the upper surface of the top plate 24. The applied protective film 76 is of a thickness so as to make the upper surface of the front face 18 flat.

The front face cover 70 has opposite end portions, which are formed as sides (first sides) 78 that extend in the direction of the arrow Z1, and are erected substantially from the front face cover 70. The rear face 20 has a bottom plate 80 opposite to the top plate 24, and sides (second sides) 82 that extend from opposite end portions of the bottom plate 80 in the direction of the arrow Z2, and are erected substantially from the bottom plate 80. The front face 18 is fitted over the rear face 20 such that the sides 82 of the rear face 20 are positioned inside of the sides 78 of the front face cover 70.

According to the present embodiment, the sides 82 are positioned entirely inside of the sides 78. However, only portions of the sides 82 may be positioned inside of the sides 78.

As shown in FIGS. 4 and 5, the sides 78, 82 include screw holes 84, 86, which are defined respectively therein and extend in the direction of the arrow Y. While the sides 78, 82 are fitted together with the screw holes 84, 86 being substantially aligned coaxially with each other, screws 88 that serve as fastening members are threaded into the screw holes 84, 86 in the direction of the arrow Y in order to fasten the sides 78, 82. The sides 78 have recesses 92 defined therein, which are connected substantially coaxially to the screw holes 84. In case that the screws 88 fasten the sides 78, 82 together, respective heads 90 of the screws 88 are housed in the recesses 92.

In case that the sides 78, 82 are fitted together and the screws 88 fasten the sides 78, 82, the front face 18 and the rear face 20 are fastened to each other along the direction of the arrow Y, thereby making up the casing 14. The casing 14, which is produced in this manner, includes a storage space 94 therein, which forms a closed space for storing the radiation conversion panel 38 and the circuit section 40, etc.

The front face cover 70 and the sides 78 of the front face 18 are joined to each other by beveled corners 96. The beveled corners 96 have shock absorbing members 98 embedded therein, which serve to protect the radiation conversion panel 38 and the circuit section 40 that are stored in the storage space 94, in the case that the casing 14 is subjected to shocks or loads applied in case that the electronic cassette 10 is dropped. According to the present embodiment, not only the corners 96, but also other corners of the casing 14 may be beveled, and shock absorbing members 98 may be embedded in such beveled corners.

Distal ends 97 of the sides 78, which are positioned at adjoining regions between the front face cover 70 and the rear face 20, and corners 99, which are positioned between the bottom plate 80 and the sides 82, also are beveled. The beveled distal ends 97 and corners 99 provide smooth edge-free curved surfaces around the side faces of the casing 14. As a result, in case that the electronic cassette 10 is inserted between the patient and the bed and is brought into contact with the patient, a soft feeling is imparted to the patient, and the electronic cassette 10 can be inserted smoothly and quickly into place.

The corners 96, 99 of the casing 14 do not represent points, but areas at which the front face cover 70 and the rear face 20 are curved in different directions.

A base plate 102 is supported in the storage space 94 by spacers 100 that are erected from the bottom plate 80. The base plate 102 is in the form of a metal table, which has a greatest flat area among the components that are housed in the storage space 94. The circuit section 40 includes a circuit board 104, which is disposed between the spacers 100 beneath a bottom surface of the base plate 102, and is fastened to the base plate 102 by screws 106. The circuit section 40 further includes a plurality of circuit parts 108 that are mounted on the circuit board 104.

The radiation conversion panel 38 is disposed in the storage space 94 between the base plate 102 and the top plate 24, and is attached to the top plate 24.

The radiation conversion panel 38 is an irradiation-side-sampling (ISS) radiation conversion panel, in which the TFT board 42 and the scintillator 44 are arranged in this order as viewed from the top plate 24 that is irradiated with radiation 12. The TFT board 42, the upper surface of which serves as the irradiation surface 45 of the radiation conversion panel 38, is attached to the bottom surface of the top plate 24. The image-capturing area 46, which is provided by the bottom surface of the TFT board 42, faces toward the rear face 20 so as to be opposite to the scintillator 44. Therefore, the irradiation surface 45, which is remote from the bottom surface of the TFT board 42 that serves as the image-capturing area 46, is irradiated with radiation 12 that has passed through the top plate 24.

According to the present embodiment, the radiation conversion panel 38 may be a penetration-side-sampling (PSS) radiation conversion panel, in which the scintillator 44 and the TFT board 42 are arranged in this order as viewed from the top plate 24 that is irradiated with radiation 12. Further, alternatively, the radiation conversion panel 38 may be a direct-conversion radiation conversion panel, which incorporates a transducer layer of amorphous selenium for directly converting radiation 12 into electric charges.

The circuit board 104 is electrically connected to the TFT board 42 by a flexible cable 110, which is laid out in the storage space 94 and extends through the base plate 102. The flexible cable 110 corresponds to the above-described scanning lines 54 and signal lines 56, for example.

As shown in FIGS. 4 and 5, as for the electronic cassette 10 and the casing 14 according to the present embodiment, inside surfaces of the corners 96 of the front face 18 in the storage space 94 are defined as corner portions 111, and water-resistant members 112, which comprise elastic members of polymer sheeting, rubber, or the like, which function as packings, are disposed respectively in the corner portions 111. The corner portions 111 in which the water-resistant members 112 are disposed preferably are arranged in positions that are held in contact with inner surfaces 113 of the sides 78. However, the corner portions 111 may be disposed in positions that are spaced from the inner surfaces 113, insofar as the water-resistant members 112 are brought into contact with the corner portions 111 and the inner surfaces 113 in case that the water-resistant members 112 are compressed by distal ends 118 of ridges 114, as will be described below.

Figure 7:
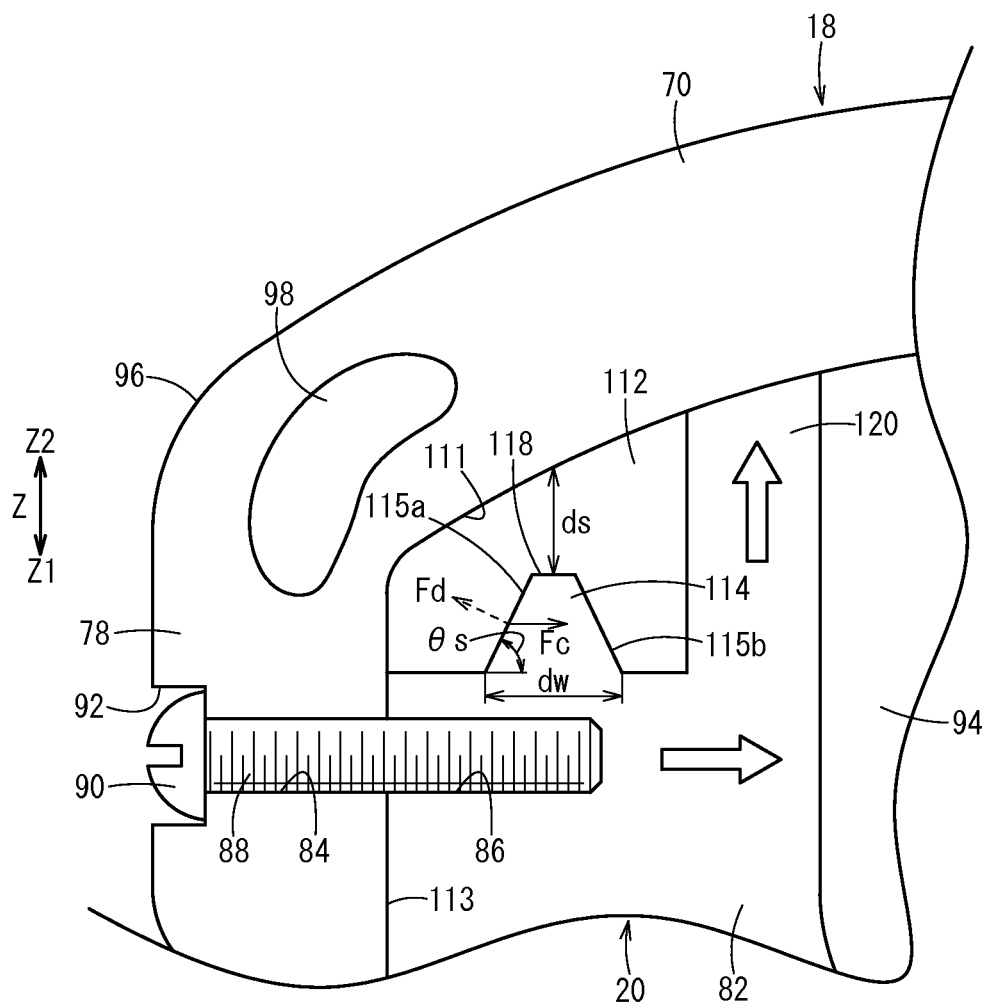
FIG. 7 is an enlarged fragmentary cross-sectional view of the side region, showing a state after the water-resistant member is compressed by the ridge and members of the side region are fastened by a screw.

The sides 82 have respective ridges 114 on distal ends thereof that face in the direction of the arrow Z2. In case that the sides 78, 82 are fitted together, the ridges 114 press and deform the water-resistant members 112 toward the front face cover 70. As shown in FIGS. 5 through 7, each of the ridges 114 has an outer side surface 115a, which faces outwardly in the direction of the arrow Y. The outer side surface 115a preferably is slanted at a gradient defined by an angle θs, such that in case that the ridge 114 presses the water-resistant member 112, the ridge 114 is capable of compressing the water-resistant member 112 effectively in both directions of the arrows Y1 and Z2.

As shown in FIGS. 5 through 7, in order for the entirety of the ridge 114 to press the water-resistant member 112, the ridge 114 is of a substantially trapezoidal cross-sectional shape, two oblique sides of which are defined respectively by the outer side surface 115a and an inner side surface 115b that faces inwardly in the direction of the arrow Y.

More specifically, as shown in FIG. 7, the angle θs at which the outer side surface 115a of the ridge 114 is slanted is defined by an angle that is formed between the outer side surface 115a and a horizontal plane along the direction of the arrow Y. The angle θs preferably is in a range from 30° to 60°, and more preferably, is 45°. The width dw of the ridge 114 along the direction of the arrow Y, including the distal end 118, the outer side surface 115a, and the inner side surface 115b, which serve as portions of the ridge 114 that come into contact with the water-resistant member 112, preferably is in a range from 0.2 mm to 3.0 mm.

In FIGS. 6A through 7, the sides 78, 82 and portions around the periphery thereof are illustrated at an enlarged scale, and are not shown in hatching.

In FIGS. 5 through 7, the outer side surface 115a and the inner side surface 115b, both of which form side surfaces of the ridge 114, are shown as being slanted at the angle θs. However, according to the present embodiment, as discussed above, at least the outer side surface 115a may be slanted at the angle θs. The inner side surface 115b may be a vertical side surface, which extends along the direction of the arrow Z, or may be a slanted side surface as shown in FIGS. 5 through 7. In the following description, however, it will be assumed that both the outer side surface 115a and the inner side surface 115b are slanted.

Each of the sides 82 includes a casing support 120, which is disposed in an inner portion at the distal end in the direction of the arrow Z2. The casing support 120 extends in the direction indicated by the arrow Z2. In case that the ridge 114 presses the water-resistant member 112 in the direction of the arrow Z2, the casing support 120 is brought into contact with the front face cover 70, thereby limiting the water-resistant member 112, which is compressed by the ridge 114, to a position corresponding to a prescribed compressed thickness ds.

More specifically, the distal end of the casing support 120 in the direction of the arrow Z2 preferably is of a shape that is complementary to the shape of the lower surface of the front face cover 70. A side surface of the casing support 120 preferably is held in sliding contact with the water-resistant member 112. Accordingly, even in case that the ridge 114 presses the water-resistant member 112 in the direction of the arrow Z2 until the casing support 120 comes into abutment against the front face cover 70, the amount by which the water-resistant member 112 is compressed by the ridge 114 is limited to the position corresponding to the compressed thickness ds, which refers to the distance between the distal end 118 and the front face cover 70 along the direction of the arrow Z.

The water-resistant member 112 is compressed by the ridge 114 in the direction of the arrow Z2, and the amount by which the water-resistant member 112 is compressed by the ridge 114 is limited by the casing support 120 to a position corresponding to the compressed thickness ds. Thus, a space, which is defined by the front face cover 70, the distal end of the sides 82, the ridge 114, and the casing support 120 in the storage space 94, can be sealed tightly.

Assembling the Casing of the Electronic Cassette

The electronic cassette 10 and the casing 14 according to the present embodiment are constructed as described above.

A process of assembling the casing 14 in order to construct the electronic cassette 10 by fitting the front face 18 and the rear face 20 together, and then fastening the front face 18 and the rear face 20 with the screws 88, will be described below with reference to FIGS. 6A through 7.

First, as shown in FIG. 6A, the water-resistant member 112 is placed in the corner portion 111 inside of the corner 96 of the front face 18. At this time, the water-resistant member 112 is maintained essentially in the shape of an undeformed block, because the water-resistant member 112 is not pressed by the ridge 114.

Next, the rear face 20 is placed immediately below the front face 18 together with the attached water-resistant member 112. After the front face 18 and the rear face 20 have been positioned with respect to each other, such that the sides 82 of the rear face 20 are positioned inside of the sides 78 of the front face cover 70, the front face 18 and the rear face 20 are displaced toward each other. For example, the rear face 20 is moved toward the front face 18.

Consequently, the sides 82 of the rear face 20 are brought into contact with the inner surface 113 of the side 78 of the front face cover 70. In this condition, in case that the rear face 20 is moved further toward the front face 18, the sides 82 slide against the inner surface 113 of the sides 78, and the distal end 118 of the ridge 114 contacts the lower surface of the water-resistant member 112.

As described above, the water-resistant member 112 is an elastic member made of polymer sheeting, rubber, or the like. Therefore, in case that the rear face 20 is moved further toward the front face 18, the water-resistant member 112 becomes elastically deformed partially under the pressing force from the distal end 118 of the ridge 114. In case that the rear face 20 is moved even further toward the front face 18, the water-resistant member 112, which has been elastically deformed partially, becomes elastically deformed fully under the pressing force from the ridge 114.

In this case, the water-resistant member 112 bears the pressing forces from the distal end 118 and the outer side surface 115a of the ridge 114. In addition, due to the side 78 and the casing support 120, the side surfaces of the water-resistant member 112 are prevented from being displaced in the direction of the arrow Y. Therefore, as shown in FIG. 6B, the water-resistant member 112 is compressed and elastically deformed in the direction of the arrow Z2 under the applied pressing forces.

Subsequently, upon the casing support 120 abutting against the lower surface of the front face cover 70, the amount by which the water-resistant member 112 is compressed by the ridge 114 is limited to the position corresponding to the compressed thickness ds. At this time, the distal end 97 of the side 78 and the corner 99 of the rear face 20 lie substantially flush with each other, and the two screw holes 84, 86 and the recess 92 are aligned substantially coaxially with each other.

Next, the screws 88 are threaded into the two screw holes 84, 86 in order to fasten the sides 78, 82 to each other. As shown in FIG. 7, the screws 88 apply a fastening force Fc, which is oriented in the direction of the arrow Y2, to the sides 78, 82. At this time, the water-resistant member 112 is pressed by the ridge 114, and is held in contact with the front face cover 70, the sides 78, 82, the ridge 114, and the casing support 120. Therefore, upon application of the fastening force Fc to the sides 78, 82, the outer side surface 115a exerts a reaction force Fd responsive to the fastening force Fc from the outer side surface 115a to the water-resistant member 112. The reaction force Fd is applied along a direction perpendicular to the outer side surface 115a.

As shown in FIG. 7, the reaction force Fd, which has a force component in the direction of the arrow Z2 and a force component in the direction of the arrow Y1, presses the water-resistant member 112 toward the lower surface of the front face cover 70. Under the reaction force Fd, the water-resistant member 112 seals the gap between the front face cover 70 and the sides 82. In other words, the water-resistant member 112 is compressed elastically and deformed by an upward pressing force, which the water-resistant member 112 receives from the ridge 114 in case that the sides 82 move in the direction of the arrow Z2, and by upward and lateral forces produced by the reaction force Fd, thereby sealing the gap.

Thus, the casing 14 is constructed by fitting together and fastening the front face 18 and the rear face 20 to each other by the screws 88 in the direction of the arrow Y. Further, the interfitted surfaces of the front face 18 and the rear face 20 are reliably sealed by the water-resistant member 112, whereby entry of water and other foreign matter into the storage space 94 can be prevented.

Advantages of the Electronic Cassette and the Casing

With the electronic cassette 10 and the casing 14 according to the present embodiment, as described above, the ridge 114 on the distal end of the side 82 of the rear face 20 includes the slanted outer side surface 115a. In addition, the water-resistant member 112, which is disposed in the corner portion 111 inside of the corner 96 of the front face 18, is pressed toward the front face cover 70, and is compressed elastically and deformed by the ridge 114. More specifically, according to the present embodiment, the ridge 114 has a sloping or slanted outer side surface 115a, and the water-resistant member 112, which is disposed in the corner portion 111, is compressed toward the front face cover 70 by the gradient of the outer side surface 115a. Therefore, the water-resistant member 112 is capable of maintaining the water-resistant condition of the casing 14, even though the water-resistant member 112 is comparatively thin-walled and simple in structure.

The overall thickness of the electronic cassette 10 can be reduced by reducing the thickness of the water-resistant member 112. Consequently, in case that radiographic images of a patient who serves as a subject lying on a bed are captured using the electronic cassette 10, the electronic cassette 10 can easily be inserted between the patient and the bed with the front face 18 thereof facing toward the patient. Accordingly, the ability to insert the electronic cassette 10 is excellent.

According to Japanese Laid-Open Patent Publication No. 2000-258541, the cover and the side wall, which is erected from the end of the bottom wall of the casing, are fastened by screws along a thickness-wise direction (vertical direction) of the casing. Consequently, in case that radiographic images of a patient who serves as a subject lying on a bed are captured, the screws or the screw holes may become caught on the patient at the time the electronic cassette is inserted between the patient and the bed such that the cover thereof faces toward the patient.

With the electronic cassette 10 and the casing 14 according to the present embodiment, the sides 78, 82 are kept in an interfitted condition by the screws 88 in the direction of the arrow Y along the top plate 24 and the bottom plate 80. Since the sides 78, 82 are fastened together by the screws 88 in a lateral or horizontal direction, i.e., the direction of the arrow Y, perpendicular to the thickness-wise direction of the casing 14, which is indicated by the arrow Z, the top plate 24 that is placed in contact with the patient is free of surface irregularities. Consequently, the electronic cassette 10 can be inserted between the patient and the bed without causing the screws 88 to become caught on the patient. Owing thereto, the ability to insert the electronic cassette 10 is increased.

Inasmuch as the outer side surface 115a of the ridge 114 is slanted, as described above, in case that the sides 78, 82 are fastened together by the screws 88, the reaction force Fd, which is caused by the fastening force Fc acting on the sides 78, 82, is exerted on the water-resistant member 112. Consequently, the water-resistant member 112 is effectively compressed toward the front face cover 70. Thus, the water resistance of the casing 14 is increased by fastening the sides 78, 82 with the screws 88.

In the electronic cassette 10, the casing support 120, which extends from the side 82 in the direction of the arrow Z2, is disposed in the vicinity of the water-resistant member 112. In case that the ridge 114 presses the water-resistant member 112 toward the front face cover 70, the casing support 120 is brought into contact with the front face cover 70, thereby limiting the amount by which the water-resistant member 112 is compressed by the ridge 114 to a position corresponding to the prescribed compressed thickness ds. Since the casing support 120 supports the front face 18, even in case that the front face 18 is placed under the weight of the patient's body, deformation of the front face 18 is prevented from adversely affecting the amount by which the water-resistant member 112 is compressed.

In case that the angle θs of the outer side surface 115a lies in a range from 30° to 60°, the ridge 114 can effectively compress the water-resistant member 112. In particular, in case that the angle θs of the outer side surface 115a is 45°, the ridge 114 can more effectively compress the water-resistant member 112. Assuming that the angle θs lies in the range from 30° to 60°, the force component directed toward the front face cover 70, i.e., the component of the pressing force in the direction of the arrow Z2, which is applied from the ridge 114 to the water-resistant member 112, is increased. Therefore, the ridge 114 can effectively compress the water-resistant member 112.

In case that the width dw of the portion of the ridge 114 that contacts the water-resistant member 112, i.e., the width along the direction of the arrow Y of the ridge 114 including the distal end 118, the outer side surface 115a, and the inner side surface 115b, is in a range from 0.2 mm to 3.0 mm, the ridge 114 can effectively compress the water-resistant member 112. Since the width of the water-resistant member 112 is comparatively small, the irradiation surface 45 and the image-capturing area 46 of the electronic cassette 10 are enlarged up to positions proximate the side edges of the casing 14.

In case that the width dw is 0.2 mm or greater, the area of the ridge 114 that presses the water-resistant member 112 is increased, so that the ridge 114 appropriately compresses the water-resistant member 112 to achieve a desired water-resistant capability. On the other hand, in case that the width dw is 3.0 mm or less, it is easier for a space to be provided so that the ridge 114 can be accommodated in the storage space 94 in the interior of the casing 14.

The top plate 24 preferably is made of carbon or a resin that is permeable to radiation 12. The top plate 24, which is made of carbon or resin, allows the casing 14 to be constructed in a simple shape, makes the casing 14 more permeable to radiation 12, and is effective at reducing the thickness of the casing 14. In other words, the top plate 24, which is made of a lightweight and highly rigid material, is prevented from becoming deformed in case that the front face 18 is placed under the load from the patient, thereby preventing the amount by which the water-resistant member 112 is compressed from being adversely affected.

The water-resistant member 112, which is in the form of an elastic member that is placed in the corner portion 111 inside of the corner 96 of the front face 18, can easily be compressed by the ridge 114.

With the above-described electronic cassette 10 and the casing 14 according to the present embodiment, the sides 78, 82 are illustrated as being fastened by the screws 88 in the direction of the arrow Y. However, the present embodiment is not limited to the illustrated fasteners. Various other fasteners apart from the screws 88 may be used, insofar as such fasteners are capable of fastening the sides 78, 82 in the direction of the arrow Y.

The ridge 114 is illustrated as having a trapezoidal cross-sectional shape with the outer side surface 115a being slanted in the form of an oblique side. According to the present embodiment, the outer side surface 115a need not necessarily be slanted along a straight line, but may be slanted in a curved shape, insofar as the outer side surface 115a can compress and elastically deform the water-resistant member 112 in case that the ridge 114 presses the water-resistant member 112.

The water-resistant member 112 need not necessarily be in the shape of a block, as shown in FIG. 6A, but may have different thicknesses at different positions rather than a uniform thickness, depending on the shape of the front face cover 70 and the shape of the ridge 114.

As illustrated, the water-resistant member 112 is disposed in the corner portion 111 along the direction of the arrow X, which is perpendicular to the sheets of FIGS. 4 through 7. However, the present embodiment is not limited to the illustrated orientation. The water-resistant member 112 may be disposed along not only the direction of the arrow X, but also along the direction of the arrow Y. Alternatively, the water-resistant member 112 may be disposed circumferentially fully around the electronic cassette 10 and the casing 14.

Modifications of the Embodiment

Modifications (first through fifth modifications) of the electronic cassette 10 and the casing 14 according to the present embodiment will be described below with reference to FIGS. 8 through 12. Parts of the first through fifth modifications, which are identical to those of the electronic cassette 10 and the casing 14 shown in FIGS. 1 through 7, are denoted by identical reference characters, and such features will not be described in detail below.

Figure 8:
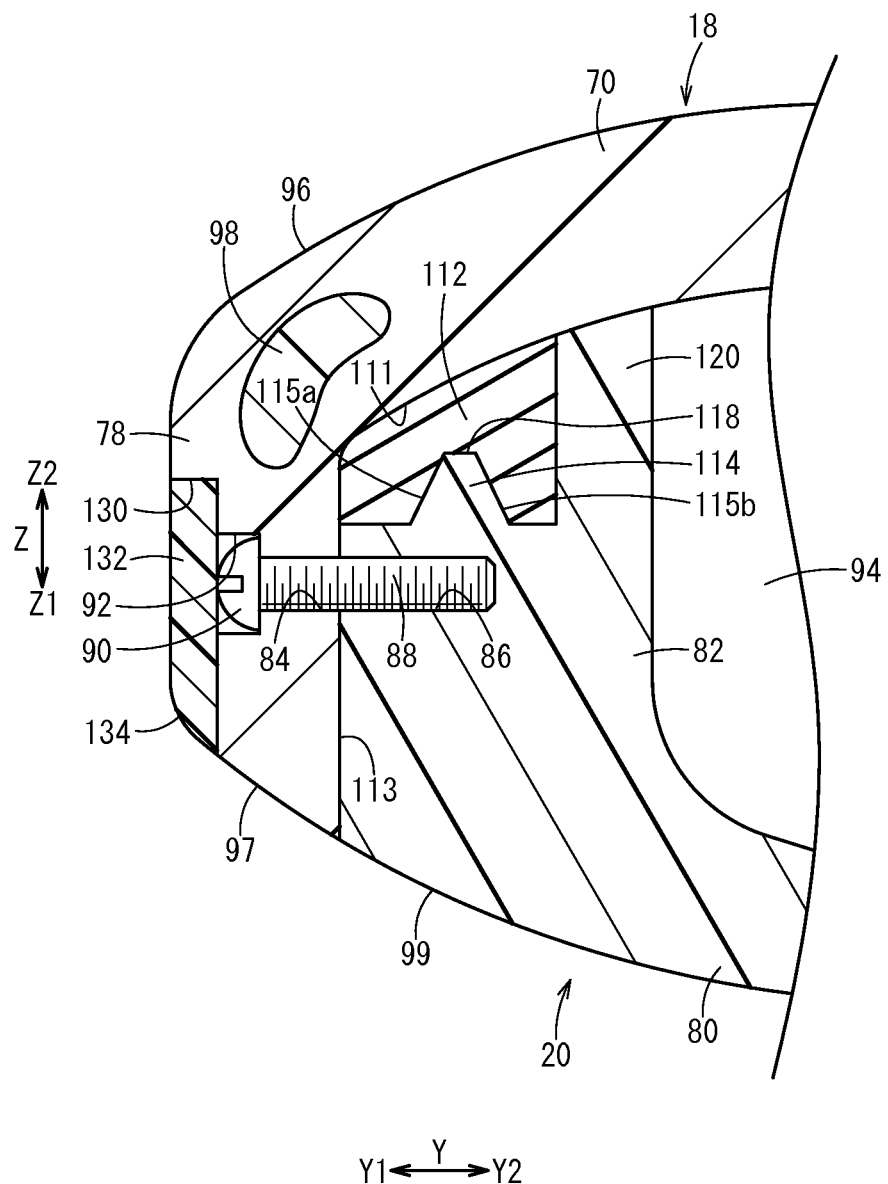
FIG. 8 is an enlarged fragmentary cross-sectional view showing a first modification of the embodiment.

According to the first modification shown in FIG. 8, the side 78 has a step 130 defined therein. An external water-resistant member 132, which serves as a seal member that covers the head 90 of the screw 88 and the recess 92, is attached to the step 130. In the first modification, the external water-resistant member 132 has a corner 134, which is beveled in order to provide smooth edge-free curved surfaces around the side faces of the casing 14.

According to the first modification, since the external water-resistant member 132 is provided that covers the head 90 of the screw 88 and the recess 92, the external water-resistant member 132 is effective to conceal the screw 88 while also increasing the water resistance of the casing 14.

According to the first modification, rather than a seal member, an adhesive may be used as the external water-resistant member 132. In case that an adhesive is used, the adhesive preferably is applied to the step 130 in order to provide smooth edge-free curved surfaces around the side faces of the casing 14.

Figure 9:
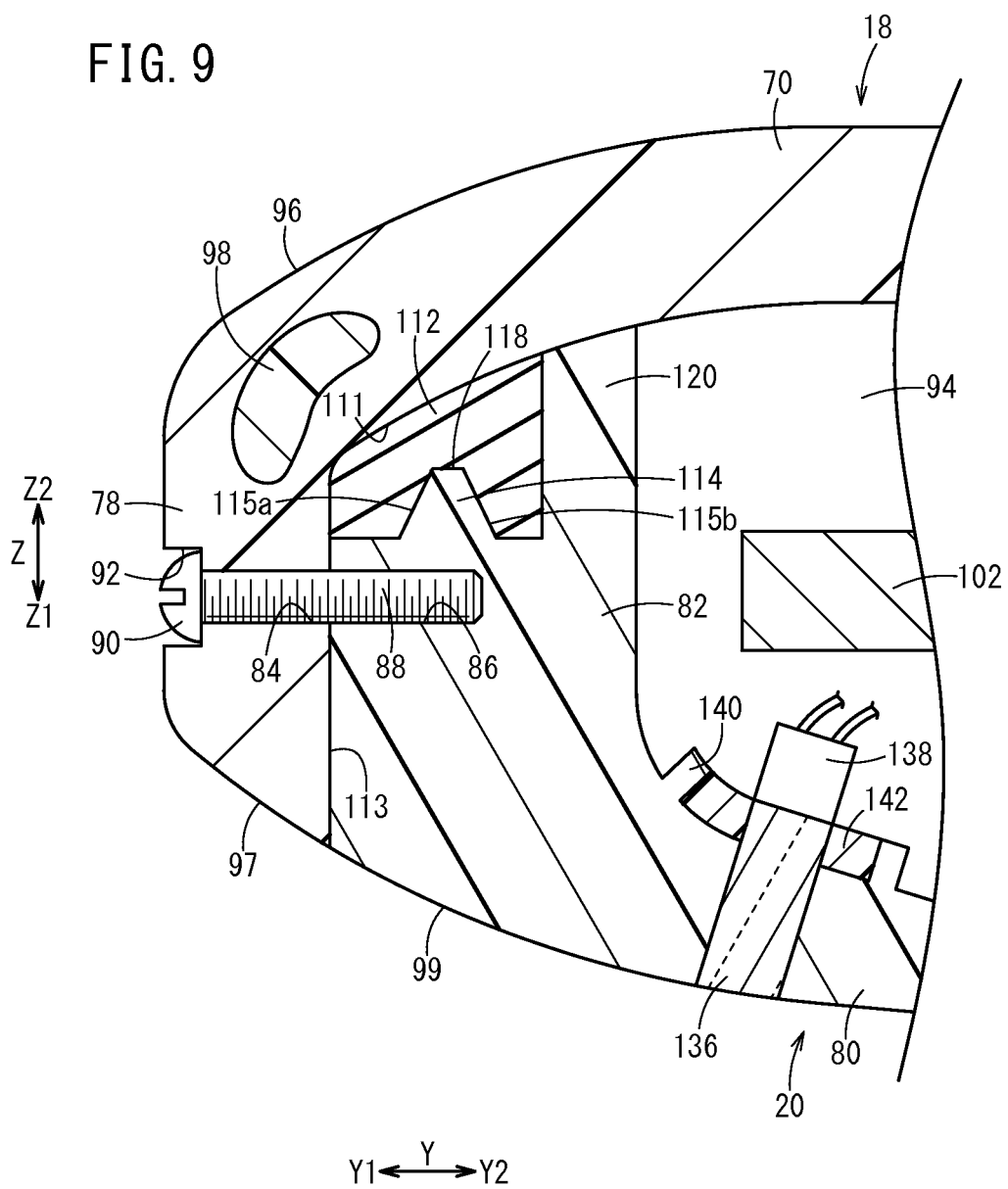
FIG. 9 is an enlarged fragmentary cross-sectional view showing a second modification of the embodiment.
Figure 10:
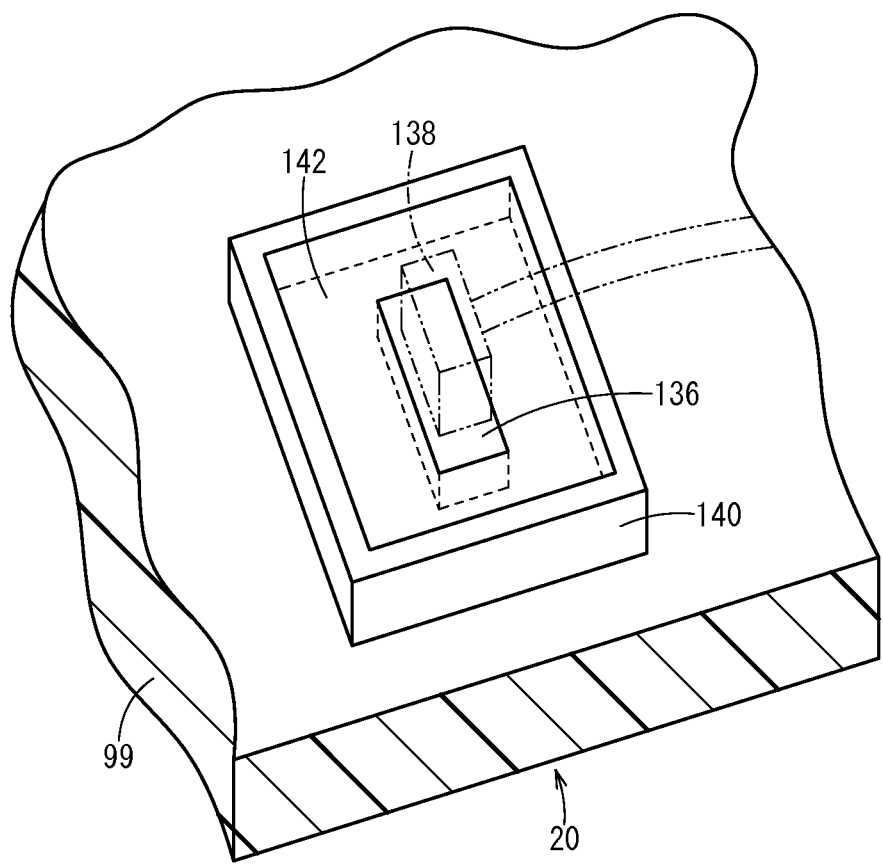
FIG. 10 is an enlarged fragmentary perspective view of a light guide, a rib, and an adhesive shown in FIG. 9, as viewed from a location within the casing.

According to the second modification shown in FIGS. 9 and 10, a light guide 136, which is made of transparent or semitransparent polycarbonate or acrylic resin, is mounted so as to extend through the corner 99 of the rear face 20. An LED 138 is disposed on the proximal end of the light guide 136 in the storage space 94. The rear face 20 has a rib 140 on a surface thereof that faces toward the storage space 94. The rib 140 surrounds the proximal end of the light guide 136 that is inserted in the storage space 94. The space surrounded by the rib 140 is filled with a transparent or semitransparent adhesive 142. The light guide 136 extends through the corner 99 of the rear face 20 and is fixed to the rear face 20. The adhesive 142 functions as a seal member for sealing the light guide 136. The adhesive 142 makes the casing 14 water-resistant while also functioning as a light guide. Accordingly, in case that the LED 138 emits light, the emitted light is transmitted outside of the casing 14 through the light guide 136 and the adhesive 142. Thus, the light guide 136 functions as an indicator.

Figure 11A:
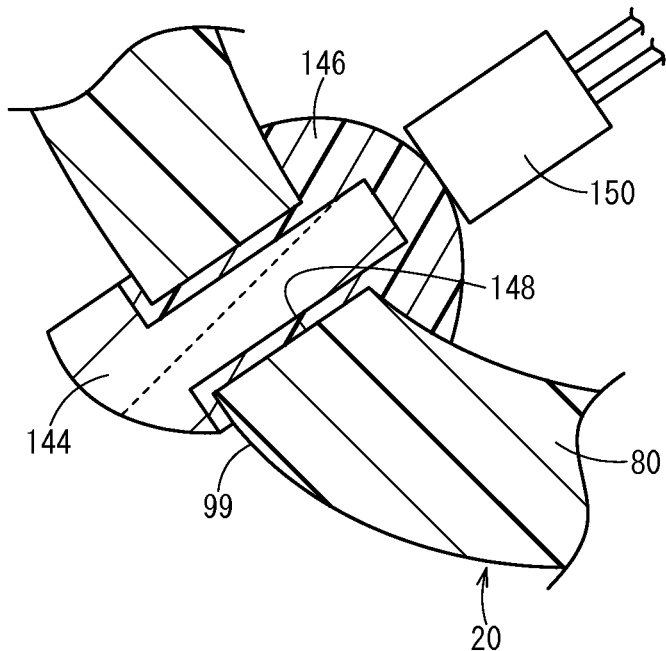
FIG. 11A is an enlarged fragmentary cross-sectional view showing a third modification of the embodiment.

According to the third modification shown in FIG. 11A, a light guide 144, which is of a substantially T-shaped cross-sectional shape and is made of the same material as the light guide 136, is disposed so as to extend through the corner 99 of the rear face 20. The light guide 144 is secured to the corner 99 by a transparent or semitransparent adhesive 146. The width of the portion of the light guide 144 that extends through the corner 99 is smaller than the diameter of a hole 148 that is defined in the corner 99 and through which the portion of the light guide 144 extends. Therefore, the adhesive 146 fills the gap between the portion of the light guide 144 that extends through the hole 148 and the surface of the corner 99 that defines the hole 148. The portion of the light guide 144 that is exposed outside of the corner 99, the portion of the light guide 144 that extends through the hole 148, and the proximal end of the light guide 144 in the storage space 94 are firmly secured by the adhesive 146 to the corner 99 of the rear face 20.

An LED 150, which is positioned in the storage space 94, is disposed in confronting relation to the proximal end of the light guide 144 by the adhesive 146. Since the light guide 144 extends through the corner 99 of the rear face 20 and is securely bonded to the corner 99 by the adhesive 146, the adhesive 146 functions as a seal member, which makes the casing 14 water-resistant and also functions as a light guide. Accordingly, in case that the LED 150 emits light, the emitted light is transmitted outside of the casing 14 through the adhesive 146 and the light guide 144. Thus, the light guide 144 functions as an indicator.

According to the third modification, the light guide 144 may be secured to the corner 99 of the rear face 20 by a transparent or semitransparent water-resistant tape, rather than the adhesive 146. Such a water-resistant tape is effective to make the casing 14 water-resistant, and also functions as a light guide.

Figure 11B:
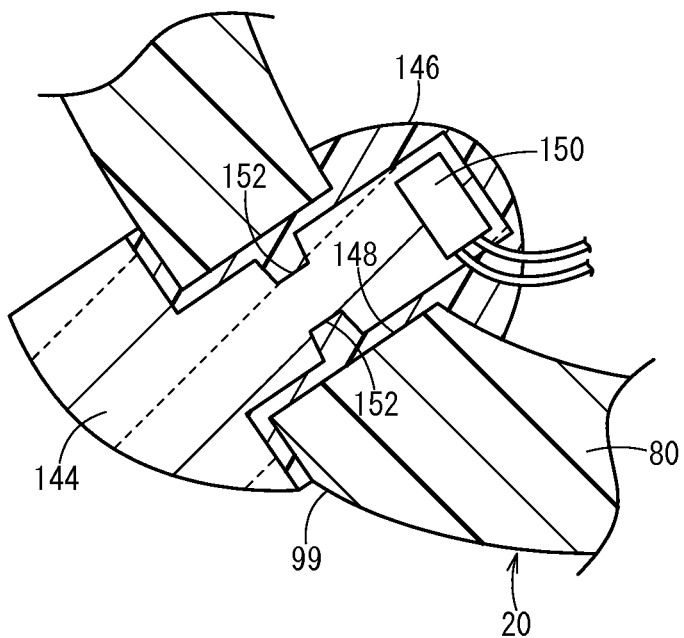
FIG. 11B is an enlarged fragmentary cross-sectional view showing a fourth modification of the embodiment.

According to the fourth modification shown in FIG. 11B, the light guide 144 includes recesses 152 defined centrally in the portion thereof that extends through the corner 99. The recesses 152 function as a trap for holding the adhesive 146. Since the portion of the light guide 144 that extends through the corner 99 is surrounded by the adhesive 146 that is held by the recesses 152, the light guide 144 is secured reliably to the corner 99 of the rear face 20. The adhesive 146 performs a better function as a water-resistant seal. Moreover, according to the fourth modification, the LED 150 is inserted in the proximal end of the light guide 144. Accordingly, in case that the LED 150 emits light, the emitted light is reliably transmitted through the light guide 144 and out of the casing 14. Thus, the light guide 144 functions as an indicator.

Figure 12:
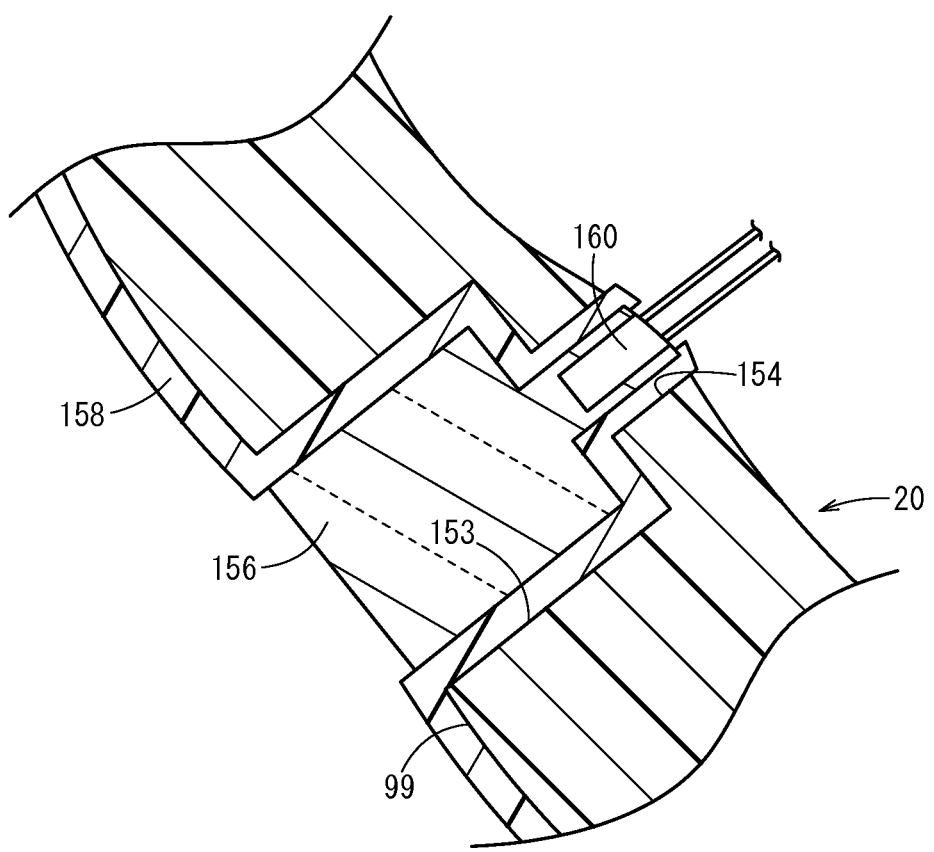
FIG. 12 is an enlarged fragmentary cross-sectional view showing a fifth modification of the embodiment.

According to the fifth modification shown in FIG. 12, the corner 99 of the rear face 20 includes a cavity 153 defined therein, which is connected to the storage space 94 through a hole 154 defined in the corner 99. A light guide 156, which is made of the same material as the light guides 136, 144, has a stepped configuration, which is complementary to the shape of the cavity 153 and the hole 154. A sheet member 158, which is sticky and water-resistant, is press-fitted into a gap provided between the light guide 156 and the surfaces that define the cavity 153 and the hole 154.

The sheet member 158 is shaped in the form of a bag that covers the corner 99 of the rear face 20, and has a portion that is pressed into and compressed in the gap between the light guide 156 and the surfaces that define the cavity 153 and the hole 154. The portion of the sheet member 158, which is compressed in the gap, is adhered to the rear face 20 by heat or ultrasonic energy, thereby ensuring water resistance in the gap between the light guide 156 and the surfaces that define the cavity 153 and the hole 154.

According to the fifth modification, an LED 160 is inserted in the proximal end of the light guide 156. Accordingly, in case that the LED 160 emits light, the light emitted from the LED 160 is transmitted reliably through the light guide 156 and out of the casing 14. Thus, the light guide 156 functions as an indicator.

According to the second through fifth modifications, the light guides 136, 144, 156 are illustrated as being secured to the corner 99 of the rear face 20 by the adhesives 142, 146 or by the sheet member 158, thereby making the casing 14 water-resistant. According to the present embodiment, the second through fifth modifications may also be applied in order to secure the battery unit 26 to the battery mount region 28, or to secure the opening of the antenna of the communication unit 66.

Although a preferred embodiment and various modifications have been described above, it should be understood that the present invention is not limited to the illustrated embodiment and modifications, but various changes may be made thereto without departing from the scope of the invention as set forth in the appended claims.

What is claimed is:

1. A portable radiographic image capturing apparatus comprising:
   a radiation conversion panel configured to output image information based on radiation applied thereto; and
   a casing housing the radiation conversion panel, wherein:
   the casing comprises a front face including a planar top plate disposed opposite to an irradiation surface of the radiation conversion panel, and a rear face that is fitted in the front face;
   the front face includes a first side that extends from an end of the top plate toward the rear face;
   the rear face includes a bottom plate disposed opposite to the planar top plate and the radiation conversion panel, and a second side that extends from an end of the bottom plate toward the top plate, the rear face being fitted in the front face such that the second side is positioned inside of the first side;
   a light guide that extends through the rear face is disposed in the rear face;
   an LED that emits light outwards through the light guide is disposed in the casing;
   a water-resistant member is disposed in a corner portion inside of a junction between the top plate and the first side of the front face;
   the second side has a ridge configured to have a trapezoidal cross-sectional shape and press and deform the water-resistant member toward the top plate;
   the ridge includes a flat distal end, a slanted outer side surface, and a slanted inner side surface; and
   the distal end, the slanted outer side surface, and the slanted inner side surface make contact with the water-resistant member.

2. The portable radiographic image capturing apparatus according to claim 1, wherein the first side and the second side are fitted together by a fastener in a direction along the top plate and the bottom plate.

3. The portable radiographic image capturing apparatus according to claim 1, further comprising:
   a casing support disposed near the water-resistant member and extending from the bottom plate toward the top plate,
   wherein in case that the ridge presses the water-resistant member toward the top plate, the casing support is brought into contact with the front face, thereby limiting an amount by which the water-resistant member is compressed by the ridge to a position corresponding to a prescribed compressed thickness.

4. The portable radiographic image capturing apparatus according to claim 1, wherein the slanted outer side surface is slanted at an angle in a range from 30° to 60°.

5. The portable radiographic image capturing apparatus according to claim 1, wherein the ridge has a portion that is held in contact with the water-resistant member, and a width of the portion is in a range from 0.2 mm to 3.0 mm.

6. The portable radiographic image capturing apparatus according to claim 2, further comprising an external water-resistant member that covers an exposed portion of the fastener.

7. The portable radiographic image capturing apparatus according to claim 1, wherein the top plate is made of carbon or a resin permeable to the radiation.

8. The portable radiographic image capturing apparatus according to claim 1, wherein the water-resistant member disposed in the corner portion is an elastic member.

9. The portable radiographic image capturing apparatus according to claim 1, wherein
   a corner that is the junction between the top plate and the first side of the front face is beveled and has a shock absorbing member embedded therein, and
   the water-resistant member is disposed in the corner portion inside of the corner.

10. The portable radiographic image capturing apparatus according to claim 1, wherein
    the first side and the second side are fitted together by a fastener in a direction along the top plate and the bottom plate,
    an exposed portion of the fastener is covered by the external water-resistant member,
    the first side has a step defined therein,
    the external water-resistant member is attached to the step, and
    a corner of the external water-resistant member is beveled.

11. A casing housing a radiation conversion panel configured to output image information based on radiation applied thereto, comprising:
    a front face including a planar top plate disposed opposite to an irradiation surface of the radiation conversion panel, and a rear face that is fitted in the front face, wherein:
    the front face includes a first side that extends from an end of the top plate toward the rear face;
    the rear face includes a bottom plate disposed opposite to the planar top plate and the radiation conversion panel, and a second side that extends from an end of the bottom plate toward the top plate, the rear face being fitted in the front face such that the second side is positioned inside of the first side;
    a light guide that extends through the rear face is disposed in the rear face;
    an LED that emits light outwards through the light guide is disposed in the casing;
    a water-resistant member is disposed in a corner portion inside of a junction between the top plate and the first side of the front face;
    the second side has a ridge configured to have a trapezoidal cross-sectional shape and press and deform the water-resistant member toward the top plate;
    the ridge includes a flat distal end, a slanted outer side surface, and a slanted inner side surface; and the distal end, the slanted outer side surface, and the slanted inner side surface make contact with the water-resistant member.

* * * * *